United States Patent [19]
Nabeshima et al.

[11] Patent Number: 5,969,351
[45] Date of Patent: Oct. 19, 1999

[54] MASS SPECTROMETER

[75] Inventors: Takayuki Nabeshima, Kokubunji; Minoru Sakairi, Tokorozawa; Yasuaki Takada; Yukiko Hirabayashi, both of Kokubunji; Hideaki Koizumi, Tokyo, all of Japan

[73] Assignee: Hitachi, Ltd., Tokyo, Japan

[21] Appl. No.: 08/796,548

[22] Filed: Feb. 6, 1997

[30] Foreign Application Priority Data

Feb. 7, 1996 [JP] Japan .................................. 8-020922
Apr. 25, 1996 [JP] Japan .................................. 8-104909

[51] Int. Cl.⁶ .................................................. H01J 49/28
[52] U.S. Cl. .............................................................. 250/288
[58] Field of Search .................................... 250/288, 281, 250/282, 423 R

[56] References Cited

U.S. PATENT DOCUMENTS

| | | | |
|---|---|---|---|
| 5,051,583 | 9/1991 | Mimura et al. | 250/288 |
| 5,103,093 | 4/1992 | Sakairi et al. | 250/288 |
| 5,170,052 | 12/1992 | Kato | 250/288 |
| 5,581,081 | 12/1996 | Kato et al. | 250/288 |
| 5,663,560 | 9/1997 | Sakairi et al. | 250/288 |
| 5,668,370 | 9/1997 | Yano et al. | 250/288 |

FOREIGN PATENT DOCUMENTS

4-172245 6/1992 Japan .

*Primary Examiner*—Kiet T. Nguyen
*Attorney, Agent, or Firm*—Fay,Sharpe,Beall,Fagan,Minnich & McKee

[57] ABSTRACT

A semi-micro liquid chromatograph/mass spectrometer apparatus has an ion source. The space from the end portion of a flow passage of a liquid chromatograph shell to a vaporization portion is closed so as to prevent the inflow of a gas from outside the ion source into the space. Further, the nebulization and vaporization portions are joined together and heated by a common heater. Dilution of a sample to be analyzed is prevented, and high sensitivity detection becomes possible in a low velocity liquid chromatograph/mass spectrometer.

13 Claims, 10 Drawing Sheets

MASS SPECTROMETER

FIELD OF THE INVENTION

The invention relates to a mass spectrometer including an interface such as a liquid chromatography/mass spectrometer apparatus (hereinafter abbreviated to "LC/MS") effective for the isolation and analysis of a sample.

BACKGROUND OF THE INVENTION

The LC/MS has been widely used in the field of chemical analysis. In an apparatus for conducting measurement by an LC/MS, a sample in a liquid state is ionized at atmospheric pressure and is then introduced into a mass spectrometer that is placed in a vacuum. One of the main ionization methods used for this purpose is an atmospheric pressure chemical ionization method (hereinafter abbreviated to "APCI"). An example of an APCI method is described in Japanese Patent Laid-Open No. 172245/1992.

Figure 8:
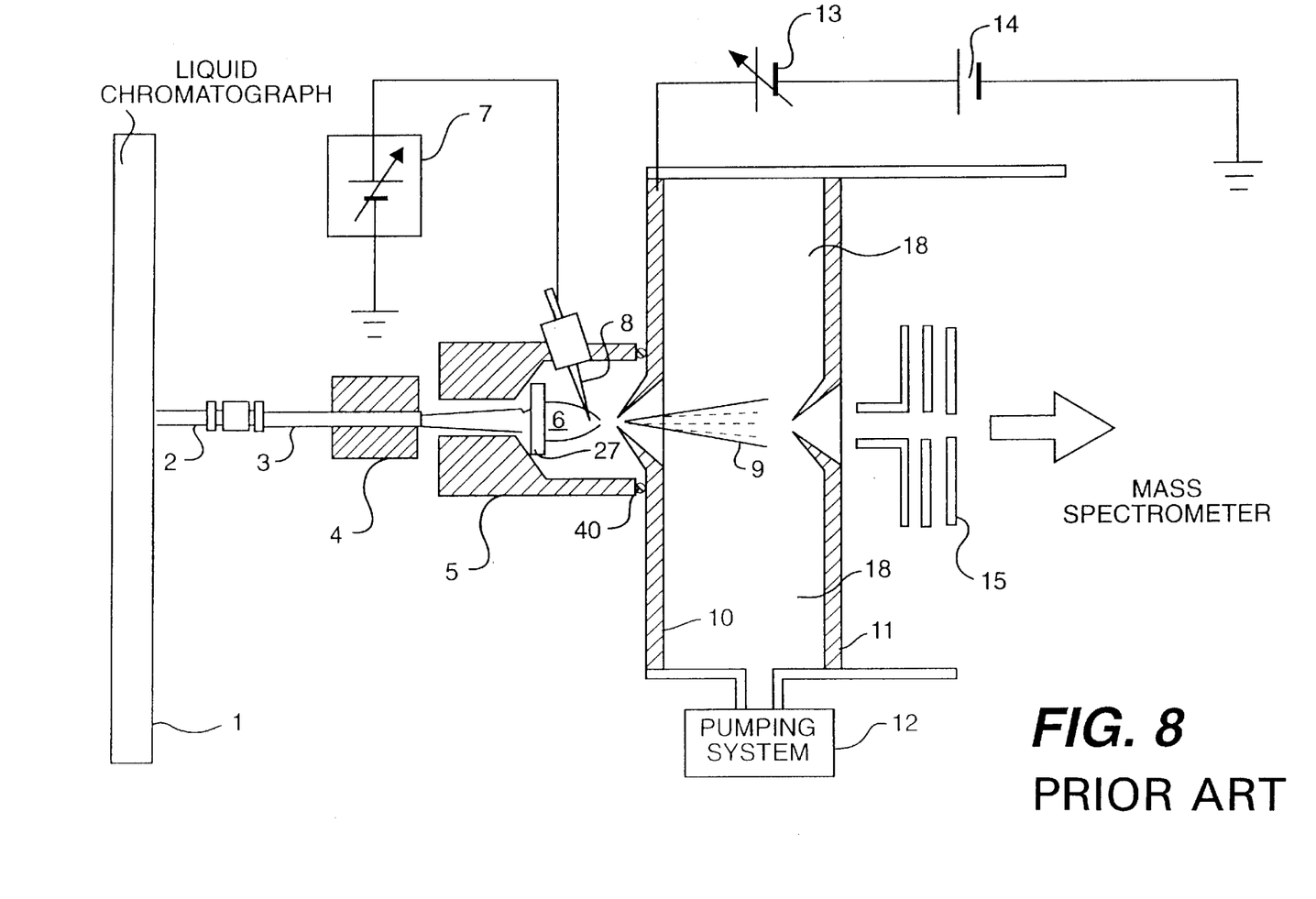
FIG. 8 is a schematic structural diagram of an LC/MS apparatus according to the prior art.

FIG. 8 schematically shows a typical structure of an ion source used in an APCI method (hereinafter referred to as an APCI ion source). A sample in the liquid chromatograph 1 is introduced with a solvent as a mobile phase through a Teflon tube 2 and a stainless steel capillary 3 into a nebulization region 4 that is heated to 200 to 400° C. The sample is nebulized in the nebulization region 4 and is then sent to a desolvation chamber 5 having a vaporization region. The desolvation chamber 5 is fixed to a first electrode 10 through an O-ring 40 for maintaining a vacuum seal. The desolvation chamber 5 is heated to about 400° C., and this heat is used as the heat of vaporization of the sample 6.

Next, the sample 6 with solvent is sent into a corona discharge space having a needle electrode 8 to which a high voltage is applied by a power supply 7 for the corona discharge. A plate 27 is positioned to close a portion near the center of the passage through which the sample and solvent flow. The plate has orifices about its periphery and is disposed at the inlet of the corona discharge space in order to prevent large charged droplets from being directly introduced into ion intake orifices in the first electrode 10. In this corona discharge space, primary ionization of the solvent molecules occurs and the sample is subsequently ionized by the ion-molecule reaction.

The resulting ions 9 are sent into a differential pumping region 18 formed between the first and second electrodes 10 and 11 and pumped down by a pumping system 12, through the ion intake orifices. An ion acceleration voltage is applied to each of the first and second electrodes 10, 11 by respective power supplies 13, 14. The ions thus accelerated pass through the ion intake orifices in the second electrode 11, are then focused by an ion focusing lens 15 and are thereafter sent to a mass spectrometer, as shown by the arrow.

Besides an APCI ion source method using heating for nebulizing the sample, there is also a method that uses gas nebulization. The construction of a typical gas nebulization apparatus is shown schematically in FIG. 9. A sample in the liquid chromatograph 1 is introduced with a solvent through a Teflon tube 2 and a stainless steel capillary 3 in a mobile phase into a nebulization region 4 through which a nebulization gas 16 flows. After being nebulized at atmospheric pressure, the sample is sent into a desolvation chamber 5 through which a vaporization gas 17 flows. The desolvation chamber 5 is fixed to the first electrode 10 through an O-ring 40, which is made of a rubber for example, for maintaining a vacuum seal. The desolvation chamber 5 is heated to about 150° C., and this heat is used as the heat of vaporization of the sample 6.

Figure 9:
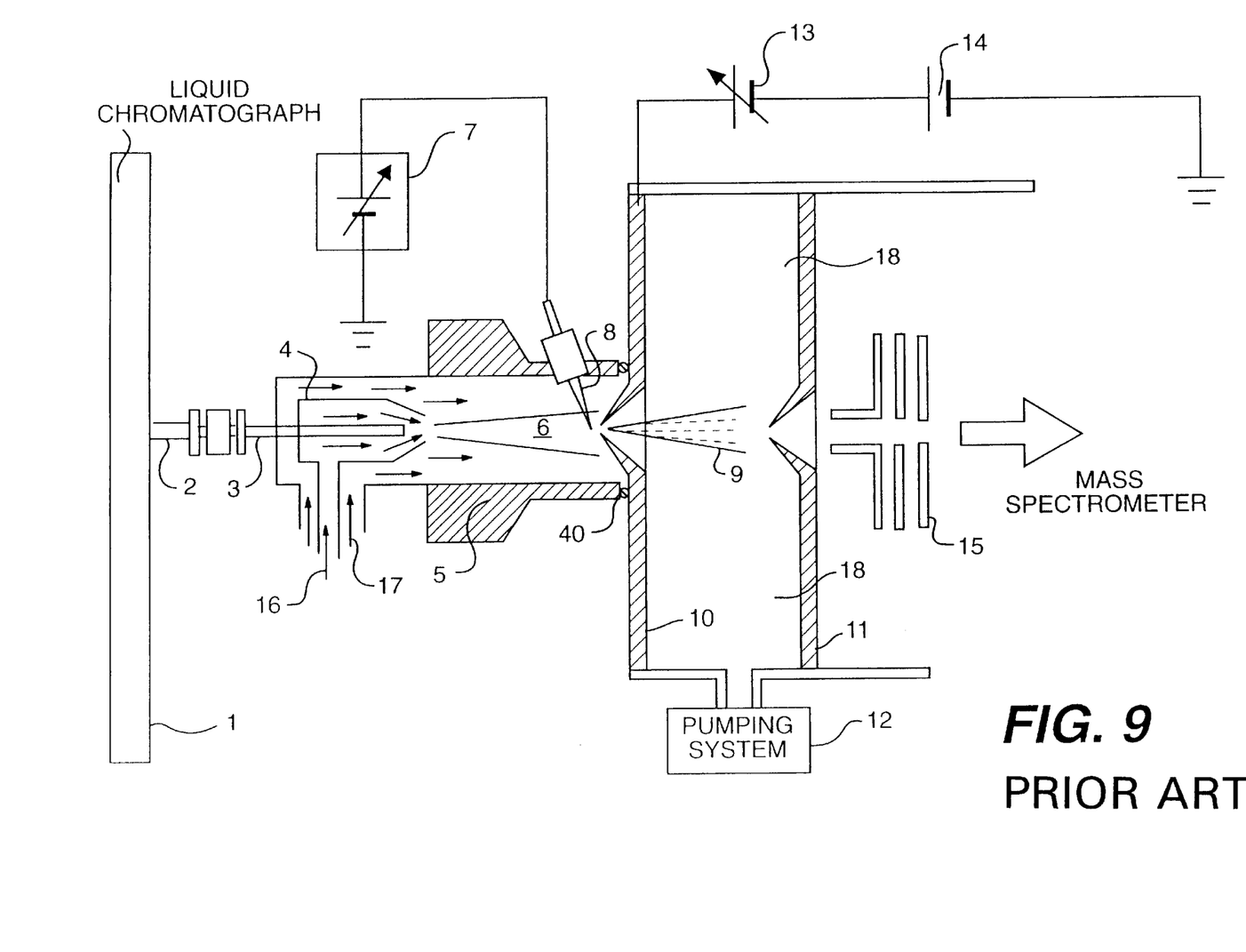
FIG. 9 is a schematic structural diagram of another LC/MS apparatus according to the prior art.

Next, the sample 6 with solvent is sent into the corona discharge space having a needle electrode 8 to which a high voltage is applied by the power supply 7. Primary ionization of the solvent molecules occurs in this corona discharge space, and the sample is subsequently ionized by the ion-molecule reaction. The resulting ions are sent into the differential pumping region 18 encompassed by the first and second electrodes 10 and 11 and pumped down by the pumping system 12, through ion intake orifices in the first electrode 10. An ion acceleration voltage is applied to each of the first and second electrodes 10, 11 from the respective power supplies 13, 14. The ions 9 are accelerated so as to pass through the ion intake orifices in the second electrode 11, are then focused by the ion focusing lens 15 and are thereafter sent to the mass spectrometer, as indicated by the arrow.

SUMMARY OF THE INVENTION

The liquid chromatograph according to the prior art described above has been used at a mobile phase flow velocity of about 1–2 ml/min. It has been found out recently, however, that measurement with a higher isolation capacity can be made by miniaturizing an isolation column of the liquid chromatograph and lowering the flow velocity of the mobile phase.

Therefore, the development of a semi-micro liquid chromatograph having a mobile phase flow velocity of about 0.1 to 0.2 ml/min has recently been persued. Since this method can reduce the introduction quantity of the sample and at the same time, can also reduce the amount of the solvent used for the mobile phase, it has attracted increasing attention. However, when this semi-micro LC is connected to an MS, the intensity of the detected ions drastically drops since the flow velocity of the mobile phase is lowered while using a conventional APCI ion source. This is because the ionization method in the conventional APCI ion source is not suitable for the interface of the LC/MS using a semi-micro liquid chromatograph.

With an APCI ion source, the molecules in the atmosphere are ionized by utilizing the corona discharge, the solvent molecules and the molecules of the mobile phase are then ionized by utilizing the reaction with these ions, and the sample is subsequently ionized by the ion-molecule reaction. This reaction time is sufficiently shorter than the time each particle stays in the ion source. Assuming the same ion source is used and that the loss of the sample enroute from the elution outlet of the liquid chromatograph to the corona discharge space (nebulization region to the desolvation space) is substantially constant, then, the intensity of the detected ions depends on the molecular concentration of the sample in the atmosphere of the corona discharge space. When the flow velocity of the mobile phase of the liquid chromatograph drops, the number of the sample molecules reaching the corona discharge space per unit time decreases. Since the ion source is assumed to be the same, the quantity of the gas flowing in from outside the ion source can be estimated as substantially equivalent. Therefore, the molecular concentration of the sample in the atmosphere of the corona discharge space is diluted. Thus, there is a drop in the intensity of the detection ions with a drop in the flow velocity of the mobile phase of the liquid chromatograph. This drop in the detected ion intensity offsets any advantage gained by using the semi-micro LC, and poses a serious problem in carrying out higher sensitivity measurement.

Because the ionization method in a conventional APCI ion source is not suitable for the interface of an LC/MS using a semi-micro liquid chromatograph, a new interface must be developed. Along these lines, the efforts to change the ion source according to the flow velocity of the LC mobile phase and to change the production process for producing the new ion source should not drastically depart from the existing technology, otherwise new problems might arise.

In addition to the foregoing problems, another problem arises with the conventional technology. Namely, if the sample is a thermally unstable compound, the temperature of the metal block that constitutes the nebulization region 4 and the desolvation chamber 5 must be kept at a low temperature in order to prevent the thermal decomposition of the sample. Under such a condition, the droplets formed by nebulization cannot be vaporized sufficiently. Consequently, there is the potential for the solution (mainly, the solvent) to condense on the needle electrode 8 if the analysis is continued for a long time. Once condensation occurs on the needle electrode, the discharge becomes unstable and stable measurement becomes difficult to conduct. Furthermore, a safety problem arises due to the possibility of a short-circuit and resultant high current flow occurring between the needle electrode and the metal cover that holds the needle electrode.

To overcome the problems described above, the present invention uses an ion source in which no air is introduced in the nebulizing, vaporizing and ionizing of the sample and solvent. An isolated/eluted solution from a liquid chromatograph is nebulized and the resulting droplets are vaporized without any gas mixed in from outside; and further while being heated by a common heater that is common to both the nebulizing of the isolated/eluted solution and the vaporizing of the resulting droplets.

The present invention, in a preferred embodiment thereof, also includes at least one plate (which closes a portion near the center of its passage and is equipped with orifices about its periphery, and which has been used in the prior art for different purposes) to sufficiently promote nebulization and desolvation and to prevent a drop in vaporization efficiency, along a path extending from an elution portion of the isolated and eluted solution of the liquid chromatograph (capillary discharge) to the corona discharge space.

The ion source according to the present invention can be substituted for the nebulizing region of a conventional APCI ion source by inserting the distal end of the stainless steel capillary into a vaporization region to which a simple modification has been made. Since the ion source of the invention can be easily exchanged for a conventional one, there is no drastic departure from the existing technology and problems expected to be associated with the exchange of the ion sources do not occur.

DETAILED DESCRIPTION OF THE PREFERRED EMBODIMENTS

This invention relates to a mass spectrometer including an interface necessary for nebulizing, vaporizing and ionizing a small amount of a sample in a liquid solvent and for conducting the mass analysis of the sample. The present invention is useful for the chemical analysis of small amounts of compounds.

Hereinafter, preferred embodiments of the present invention will be explained with reference to the accompanying drawings.

Figure 1:
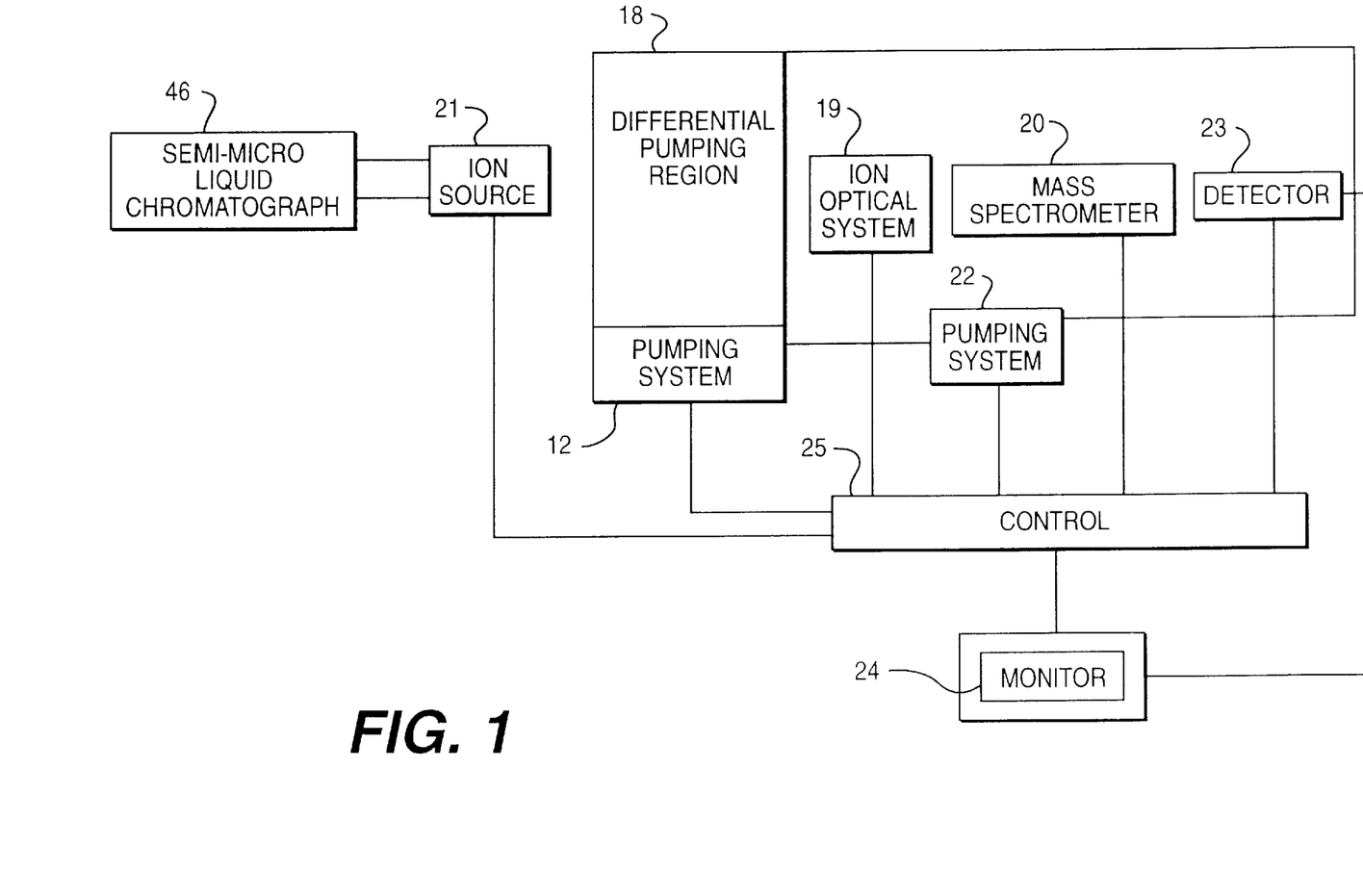
FIG. 1 is a schematic block diagram of a liquid chromotograph/mass spectrometer apparatus apparatus for practicing the present invention according to a first embodiment.

As the first embodiment, the construction of an apparatus for practicing the present invention will be explained with reference to FIGS. 1 and 2. FIG. 1 shows the overall construction of a semi-micro LC/MS according to the present invention. A sample mixed with solvent is and introduced into a semi-micro liquid chromatograph (SMLC) 46 is isolated, is sent to an ion source 21 and is ionized in the atmosphere. Ions of the sample are projected into a vacuum region pumped by a pumping system 22 through a differential pumping region 18 which is pumped by a pumping system 12. The ions of the sample pass through an ion optical system 19 and are then introduced into a mass spectrometer 20. After being analyzed by the mass spectrometer, the ions are detected by a detection portion 23 and are inspected by a monitor portion 24. Each portion of the apparatus is controlled by a control portion 25.

Figure 2:
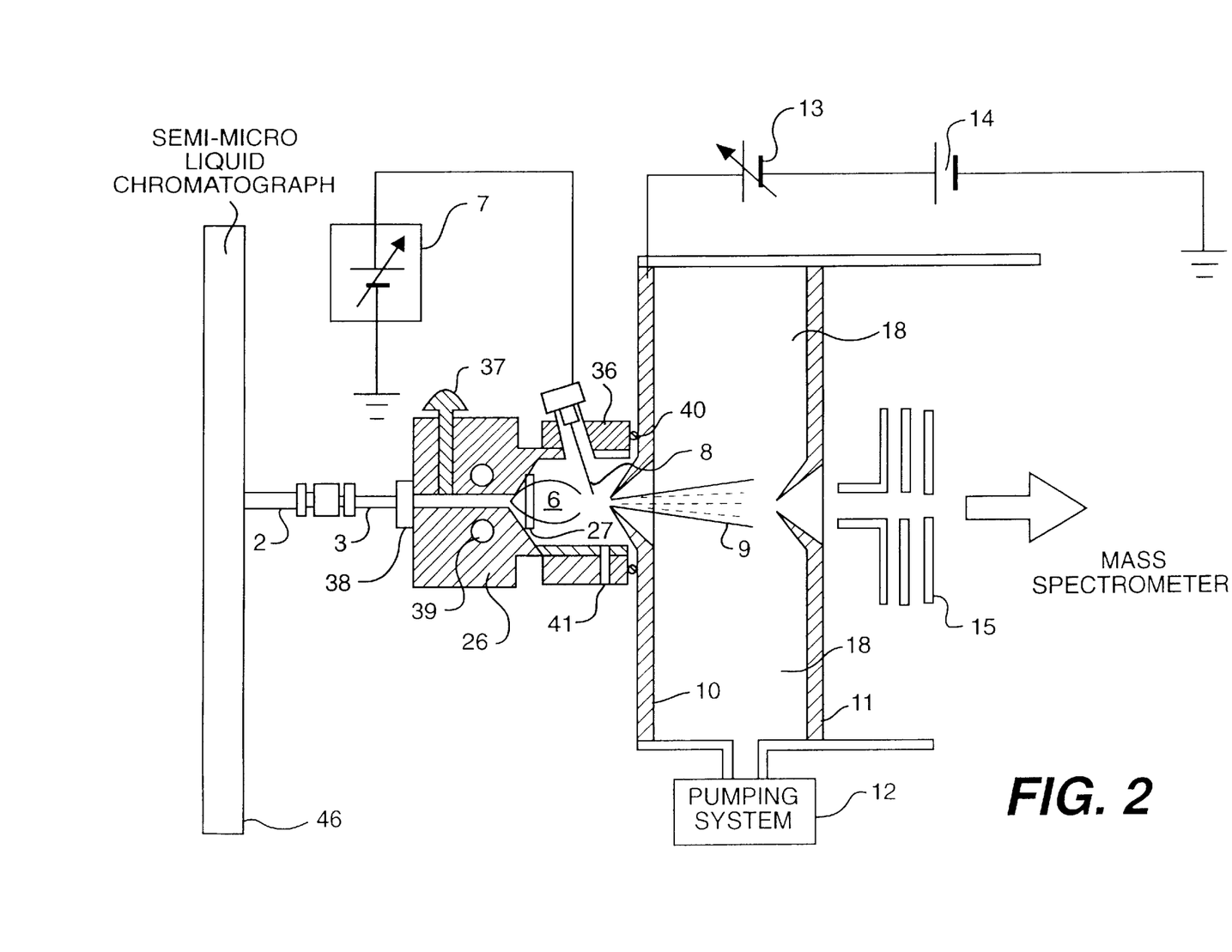
FIG. 2 is a detailed schematic structural view of a liquid chromotograph/mass spectrometer apparatus an apparatus for practicing the present invention according to the first embodiment.

FIG. 2 shows a detailed construction of portions of the ion source in the LC/MS apparatus shown in FIG. 1. The sample introduced into a semi-micro liquid chromatograph 46 is introduced with a solvent as a mobile phase into a heating portion 26 comprising a metal block (mainly made of stainless steel) that is heated to 150 to 250° C. by a cartridge heater 39 through a Teflon tube 2 and a stainless steel capillary 3. As an example, the stainless steel capillary 3 has an outer diameter of about 3 mm and an inner diameter of 0.05 to 0.25 mm. The outer diameter of the pipe is empirically determined from ease of production and thermal capacity, and the inner diameter of the pipe is also determined empirically so as to form very small droplets with a minimum possibility of clogging at its distal end.

Adjustment of the insertion length of the stainless steel capillary 3 into the heating portion 26 is a very important parameter for achieving the heating and nebulizing of a sample/solvent solution flowing through the nebulizing stage. Therefore, an adjustable stopper 38 capable of having its position varied along the capillary 3 is disposed about the outer peripheral portion thereof so that the insertion length of the capillary into the heating portion 26 can be easily adjusted. Further, when the conventional ion source shown in FIG. 8 is replaced by the ion source according to the present invention, the stainless steel capillary of the conventional apparatus can be reused and fit easily to the ion source of the present invention. On the other hand, in order to efficiently transmit the heat of the heating portion 26 to the stainless steel capillary 3 and to the solution flowing through this capillary 3, the present invention provides an adjustable level of contact between the stainless steel capillary 3 and the heating portion 26. In this embodiment, an adjustable screw 37 is disposed on the heating portion 26 so as to bring the stainless steel capillary into close contact with the heating portion 26. The cartridge heater 39 is provided as an example of a heat source for heating the heating portion 26. It may extend either parallel or orthogonal to the center axis of an orifice for emitting the ions, which opens to the orifices in the first electrode 10.

The sample 6 and the solvent are nebulized by the heating portion 26 and are passed through the orifice opening to a plate 27. Then, in a corona discharge space, a high voltage is applied by a power supply 7 to needle electrode 8 for the corona discharge. The heat of the heating portion 26 is used not only for nebulization of the solvent but also for the heat of vaporization of the solvent plus sample 6 in an atmosphere to which no additional gas is added.

Primary ionization of the solvent molecules occurs in the corona discharge space and subsequently, the sample is ionized by the ion-molecule reaction. The heating portion 26 has generally the structure as shown in the drawing, and its distal end is inserted into the metal block 36 (mainly made of the stainless steel) for holding the needle electrode 8. This is to prevent the heat of the heating portion 26, which is typically heated to a high temperature of 150 to 250° C., from being easily transferred to the metal block 36 fixed to the first electrode 10 through an O-ring 40, and in this way, deterioration of the O-ring 40 by the heat can be prevented.

The distance between the distal end of the needle electrode 8 and the ion intake orifice opening to the first electrode 10 is from 1 to 5 mm and is smaller than the distance between the distal end of the needle electrode 8 and the plate 27 so that the discharge at the distal end of the needle electrode 8 can be directed to the ion intake orifice opening in the first electrode 10. The capacity from the plate 27 to the ion intake orifice opening in the first electrode 10, in which the distal end of the needle electrode 8 exists, is 1 to 10 cm$^3$ so as to reduce the diffusion of the sample molecules inside the space, and the excessive gas is discharged outside through a hole 41 of the heating portion 26 and the metal block 36.

The ions generated in the corona discharge area pass into a differential pumping region 18 between the first and second electrodes 10 and 11 and pumped down by the pumping system 12. The ions pass through the ion intake orifice opening in the first electrode 10. An ion acceleration voltage is applied to each of the first and second electrodes 10, 11 by respective power supplies 13, 14. The accelerated ions 9 are sent into the vacuum region through the ion intake orifice opening to the second electrode 11, are focused by an ion focusing lens 15, and are then sent to the mass spectrometer. Needless to say, any of a sector type mass spectrometer, a quadrupole mass spectrometer, an ion trap type mass spectrometer and a time-of-flight mass spectrometer can be used as the mass spectrometer, according to the invention.

Figure 5:
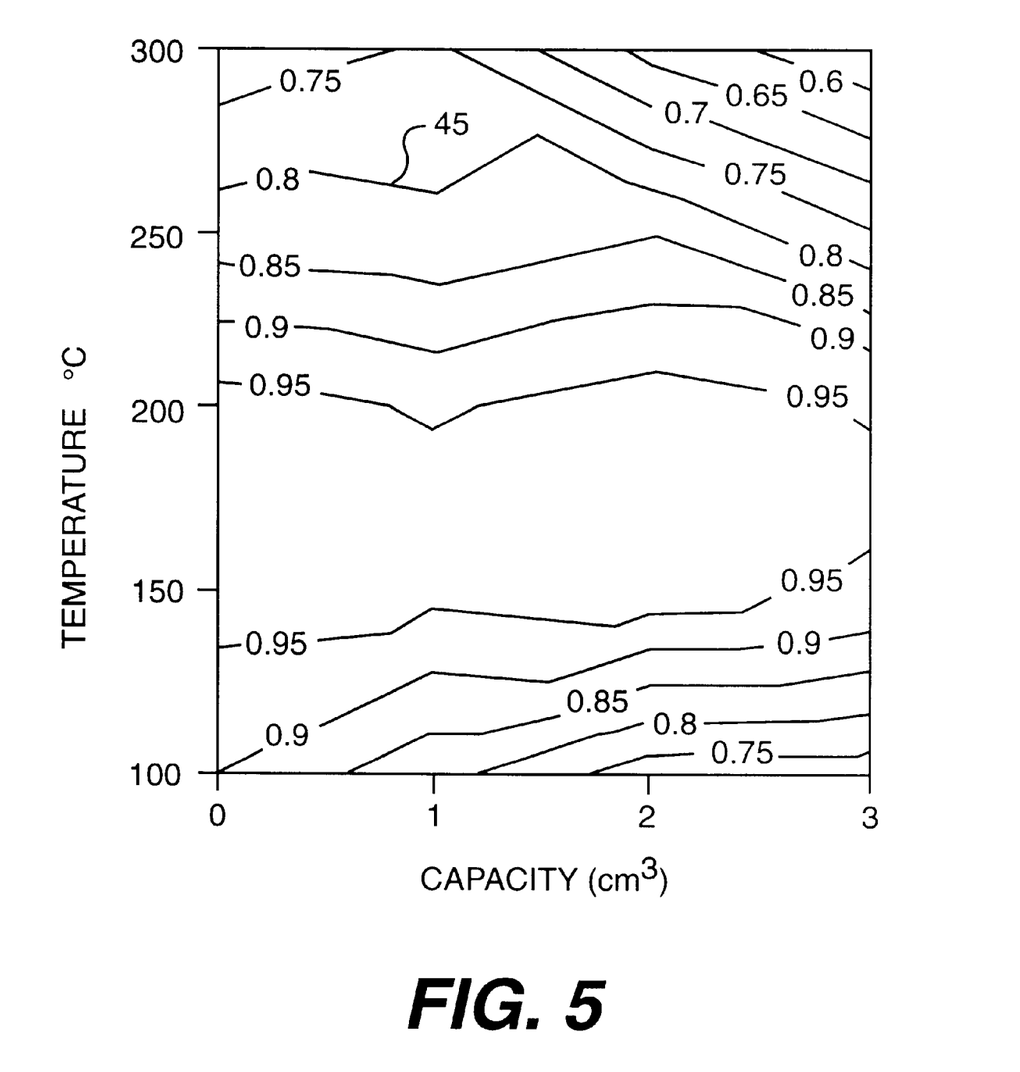
FIG. 5 is a graph showing various operating conditions for practicing the present invention according to the first embodiment.

Next, FIG. 5 shows the results of the actual measurement carried out by using the apparatus shown in FIGS. 1 and 2 and by changing two experimental conditions, that is, the capacity from the distal end of the stainless steel capillary 3 to the plate 27 (the dead volume) and the temperature of the heating portion 26. Contour lines 45 in FIG. 5 represent the result when the capacity from the distal end of the stainless steel capillary 3 to the plate 27 is plotted on the abscissa, the temperature of the heating portion 26 is plotted on the ordinate and the relative signal intensity (maximum=1, indicating maximum or 100% sensitivity) under respective conditions, of Thiuram (molecular weight=240.33 and organic pesticide) ions is plotted as the height. For these measurements, the concentration of Thiuram was 100 $\mu$mol/l, a 50% aqueous methanol solution was used as the solvent and an introduction velocity of the sample solution into the ion source was 200 $\mu$l/min. As can be appreciated from the diagram, there is an optimum range for the capacity and the temperature. In the case of Thiuram, a capacity of 0.5 to 3 cm$^3$ and a temperature range of 130 to 210° C. correspond to the optimum ranges. When the capacity deviates from this range such as when it is below 0.5 cm$^3$, vaporization efficiency of the solvent drops, so the noise increases. When the capacity exceeds 3 cm$^3$, the loss of the particles, for example by adsorption to the wall becomes great, so the sensitivity presumably drops. Also, since the temperature depends on the kind of the mobile phase and on the melting point of the sample, there may be a case depending on the measuring system, where the optimum temperature deviates from the range described above.

Figure 6:
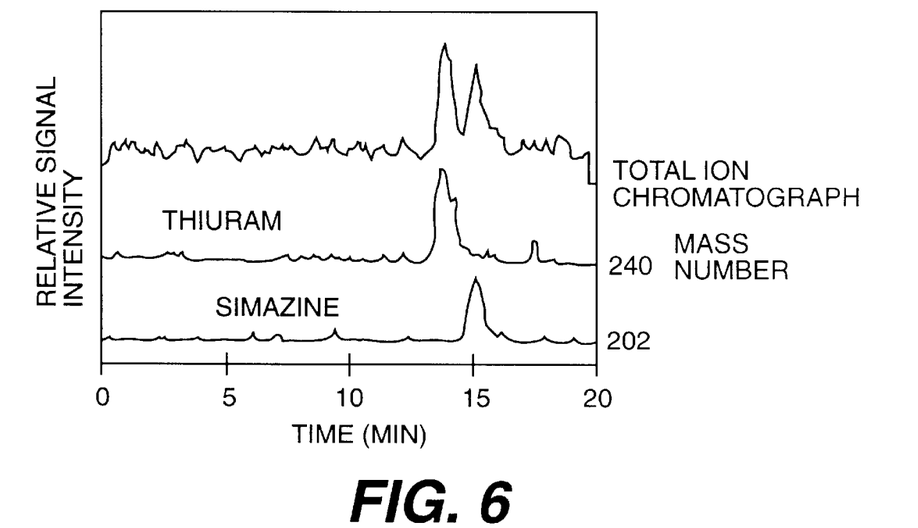
FIG. 6 is a graph showing results of analysis according to the present invention using the first embodiment.
Figure 7A:
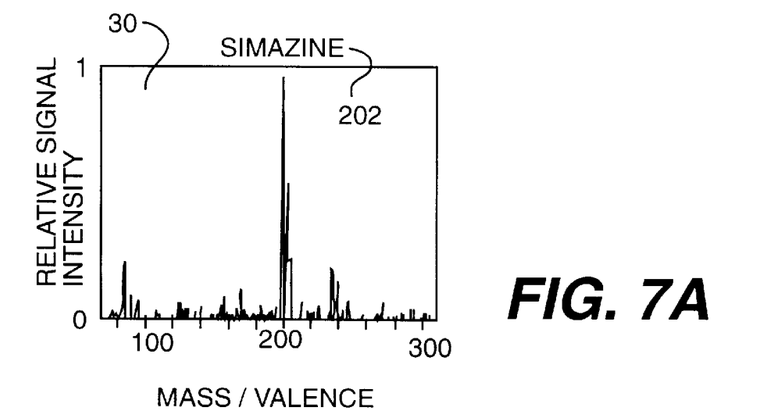
FIGS. 7A and 7B are graphs showing the practical results of the present invention.
Figure 7B:
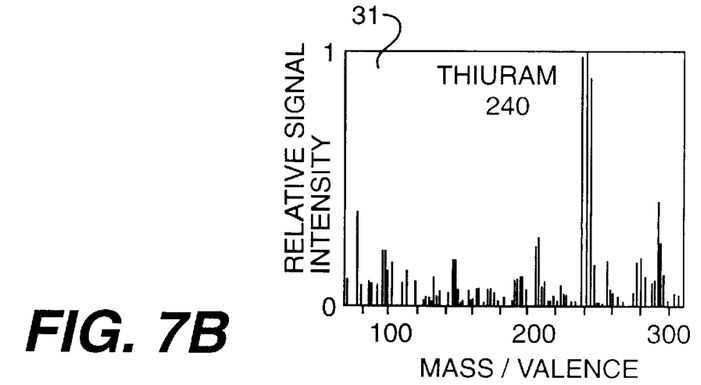

FIGS. 6 and FIGS. 7A and 7B show the results of isolation and identification of the mixed solution under the optimum condition shown in FIG. 5. The graph 29 of FIG. 6 shows the isolation result of a mixed solution of Thiuram as one of the organic pesticides (molecular weight=240.33) and Simazine (molecular weight=201.66) by the LC/MS apparatus of the invention. The graph represents the total ion chromatograph (TIC) having a mass number of 200 to 300, ions of a mass number of 240 and ions of a mass number of 202, and it can be understood that the mixed substances are isolated. FIG. 7A shows the mass spectrum 30 of Simazine and FIG. 7B shows the mass spectrum 31 of Thiuram after the isolation of the mixed substances having the chromatographs shown in FIG. 6. It can be understood from above that the two substances can be completely isolated and identified by the semi-micro liquid chromatograph/mass spectrometer of the invention.

Figure 3A:
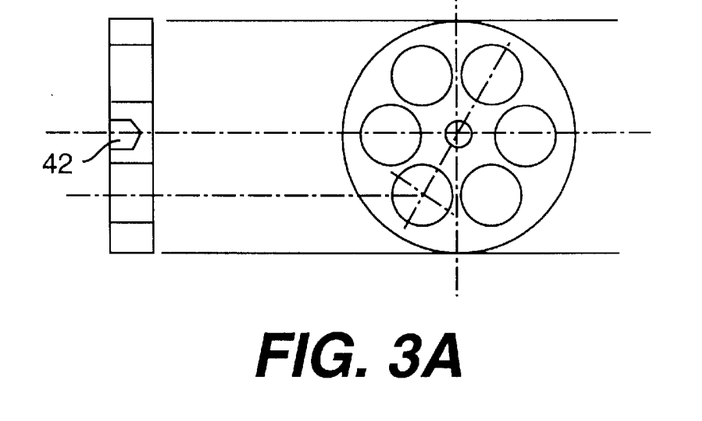
FIGS. 3A and 3B are structural views of a plate according to the present invention.
Figure 3B:
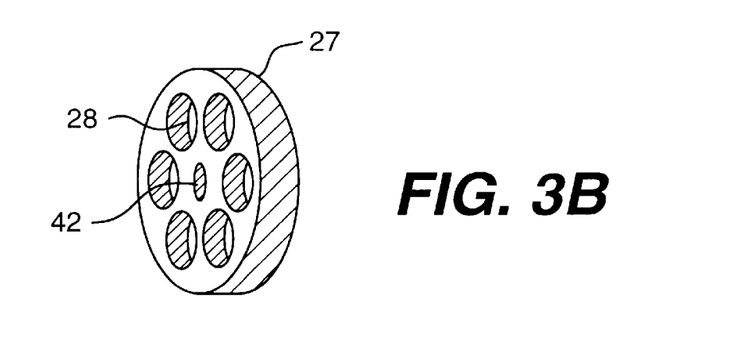

FIGS. 3A and 3B show a detailed example of the plate 27 shown in FIG. 2 according to a preferred embodiment of the present invention. The orifices 28 are disposed angularly symmetrically at six positions about the periphery of the plate with aspect to the center so as to prevent the droplets, which are accompanied by a large number of the solvent molecules due to insufficient desolvation among the droplets nebulized into the air, from directly flowing into the ion intake orifice opening in the first electrode 10. Plate 27 is heated to substantially the same temperature as the heating portion 26. The solvent and sample pass through plate 27 and impinge the side walls of the orifices 28 to receive the heat of vaporization, so that desolvation is promoted. As a result, contamination of the needle electrode can be prevented, noise can be eliminated and a drop in sensitivity can be prevented. A tap 42 is formed at the center of the plate 27. Therefore, the plate 27 can be easily removed from the heating portion 26 by driving a screw into this tap 42 from outside.

Figure 4A:
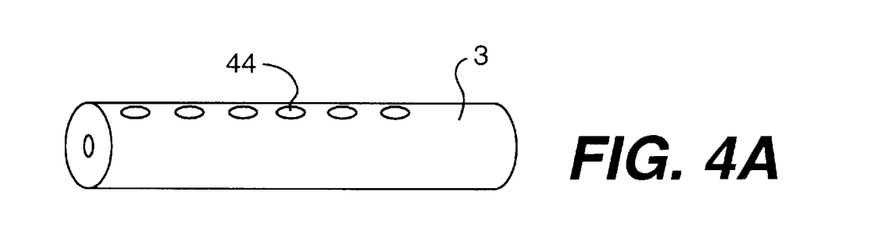
FIGS. 4A and 4B are structural views of a capillary and stopper according to the present invention.
Figure 4B:
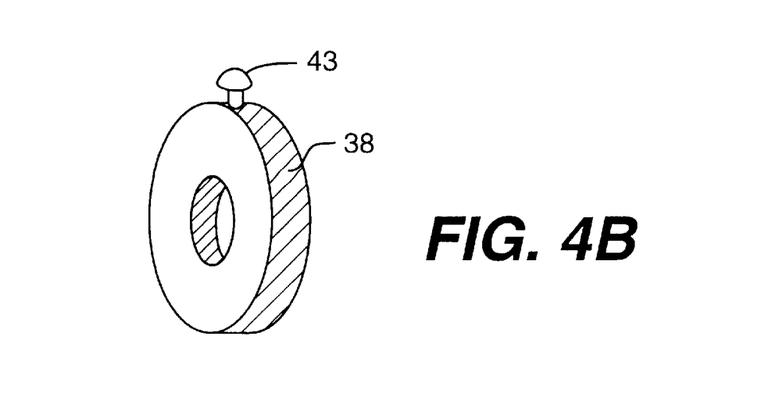

FIGS. 4A and 4B show a detailed example of the stainless steel capillary 3 and a stopper 38 shown in FIG. 2 according to a preferred embodiment of the invention. A center hole is bored in the stopper 38 and the stainless steel capillary 3 can be passed through this hole. After the stainless steel capillary 3 is passed through the hole, the stopper 38 can be fixed at an arbitrary position by a screw 43. Several taps 44 are provided along stainless steel capillary 3 which are adapted to receive screw 43 to secure stopper 38. According to this structure, the insertion length of the stainless steel capillary 3 into the heating portion can be easily changed, fixed and regulated.

Figure 10:
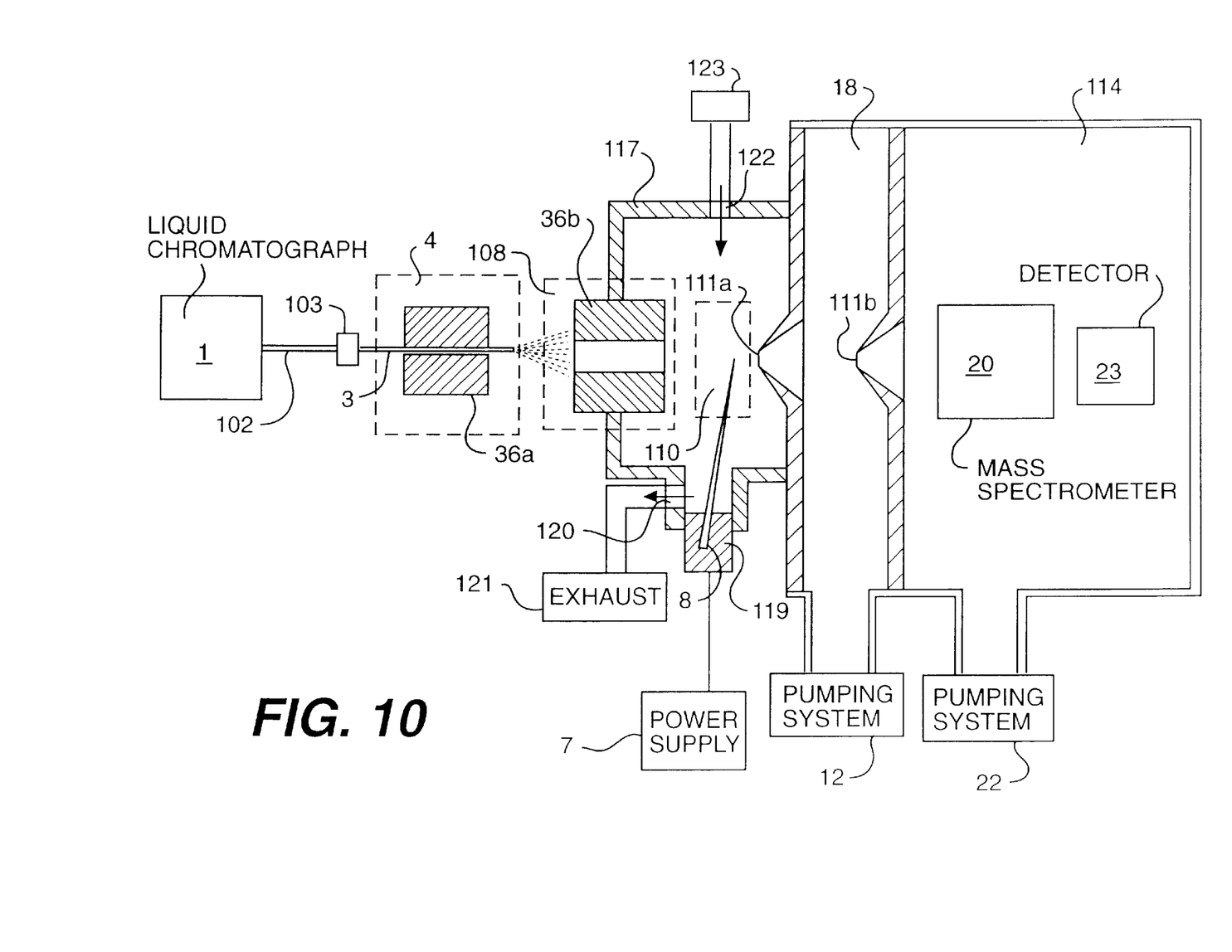
FIG. 10 is a schematic structural view of a liquid chromotograph/mass spectrometer apparatus having a discharge port for discharging solvent molecules in the proximity of a needle electrode according to a second embodiment of the present invention.

A second embodiment of the present invention will be explained with reference to FIG. 10. The sample solution sent from the liquid chromotograph 1 is introduced into the nebulization region through the piping 102 and the connector 103. The sample solution is heated and nebulized in the nebulization region 4. Droplets formed by nebulization are sent to the vaporization region 108 and are vaporized there. The gaseous sample molecules obtained by the vaporization of the droplets are introduced into the ionization region 110 within which the needle electrode 8 is disposed. A high voltage of several kilo-volts is applied to the needle electrode 8 so as to generate a corona discharge in the ionization region 110. The sample molecules react with the ions generated by the corona discharge and are ionized. The ions which are generated in such a process and relate to the sample are taken into the vacuum region 114 through the ion intake orifices 11a and 11b and the differential pumping region 18 and are then subjected to mass spectrometry by the mass spectroscope 20, which is disposed in vacuum region 114. As with the first embodiment, various types of mass spectroscopes 20 are available such as a sector type, a quadruple type, an ion trap type, and so forth. The present invention is effective regardless of the type of mass spectroscope used. After the ions mass-analyzed, they are detected by the detection portion 23, and the detected signals are processed by the data processing unit.

The metal cover 117 is disposed so as to hold the needle electrode and to prevent direct access to the high-voltage needle electrode for the purpose of safety. A discharge port 120 is provided for the metal cover 117 at a position in the proximity of the needle electrode so as to discharge the solvent molecules. Since part of the solvent molecules are discharged outside the metal cover 117 through the discharge port 120, the partial pressure of the solvent molecules inside the metal cover 117 drops and condensing of the solvent molecules on the needle electrode 8 can be prevented. Exhaust means 121 such as a fan may be provided at the discharge port 120 as shown in FIG. 10. Also, as shown in FIG. 10, it is possible to prevent condensation on the needle electrode 8 by supplying a gas such as dry nitrogen from a source 123 into the area enclosed by metal cover 117 from a blast port or jet 122 thereby lowering the partial pressure of the solvent molecules inside the metal cover 117. Furthermore, the partial pressure of the solvent molecules round the needle electrode 8 can be lowered by spraying the gas from the port 122 to the needle electrode 8, and condensation on the needle electrode 8 can be prevented.

Figure 11:
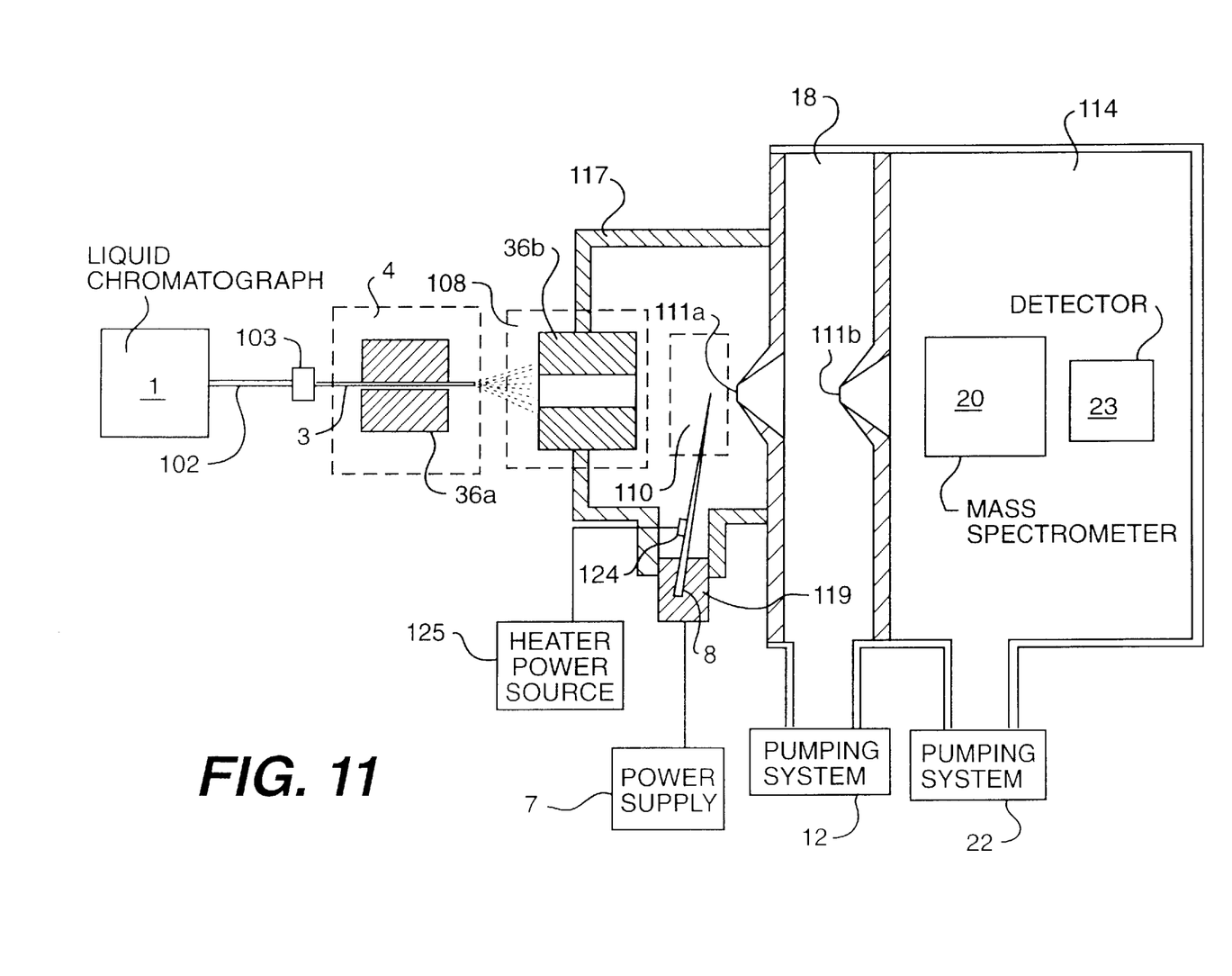
FIG. 11 is a schematic structural view of a liquid chromotograph/mass spectrometer apparatus having means for heating a needle electrode according to a third embodiment of the present invention.

A third embodiment of the present invention will be explained with reference to FIG. 11. Condensing of the solvent on the needle electrode can be prevented by keeping the needle electrode at a temperature higher than the boiling point of the solvent. In FIG. 11, a heater 124 is shown that is fit onto the needle electrode 8 so as to heat the needle electrode 8 and to keep it at a higher temperature than the boiling point of the solvent.

A high voltage of several kilovolts is applied to the needle electrode. Therefore, it may be difficult to directly fit the heater onto the needle electrode. In such a case, the heater may be disposed in the proximity of the needle electrode so as to heat the needle electrode by radiation heat. Furthermore, the needle electrode may be heated by an indirect method such as a method which fits the heater onto the metal cover to heat air that heats the needle electrode by the heat of radiation from the metal cover.

Figure 12:
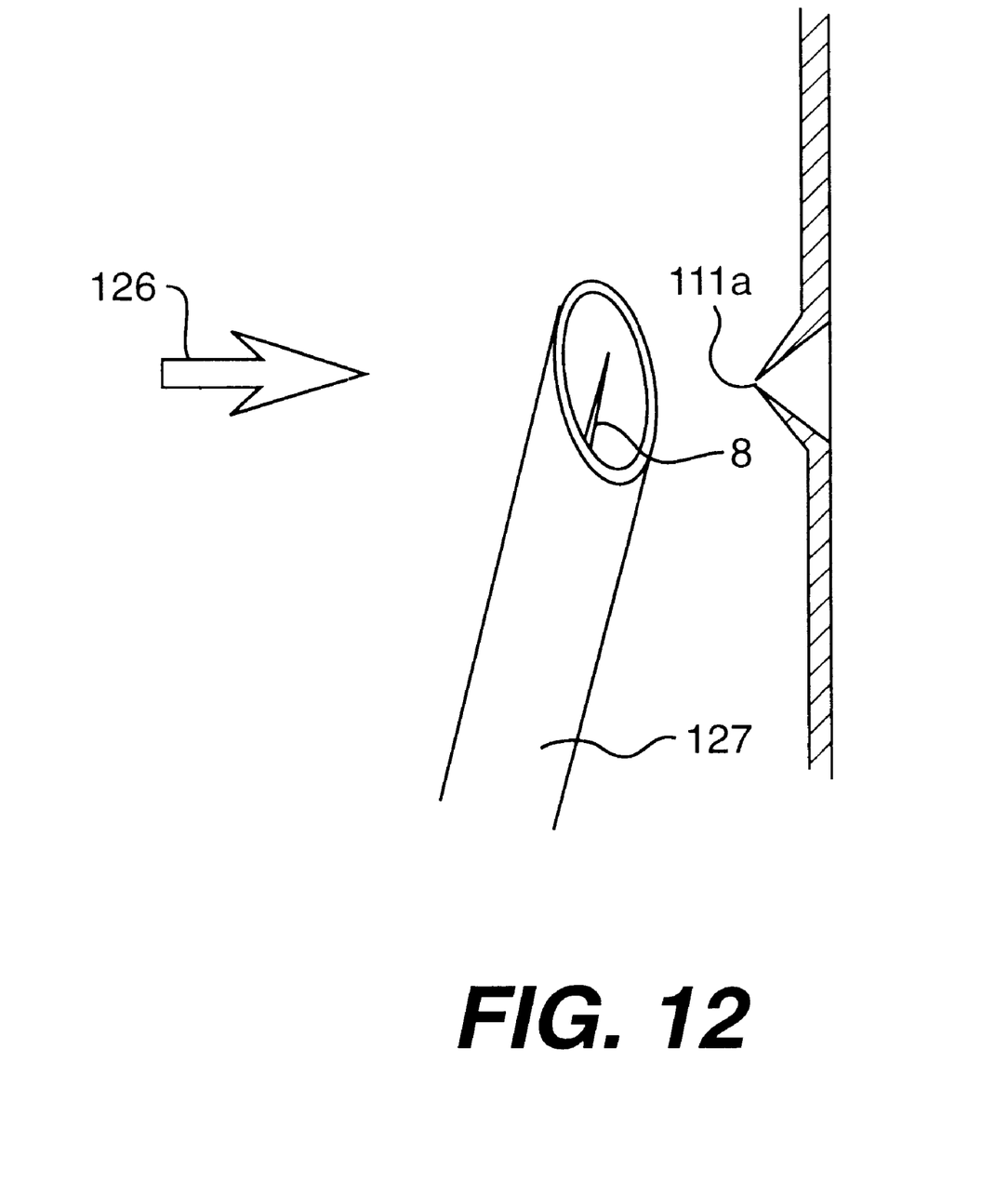
FIG. 12 is a schematic diagram showing a portion of a corona discharge space of a mass spectrometer according to the present invention having a cover for a needle electrode according to a fourth embodiment of the present invention.

An example of a fourth embodiment of the present invention will be explained with reference to FIG. 12. Condensation on the needle electrode becomes significant when the jet of the solution formed in the nebulization region is sprayed toward the needle electrode. The jet of the solution contains a large number of solvent molecules and when the jet strikes the needle electrode, the latter is cooled. Therefore, condensation on the needle electrode can be prevented by disposing a needle electrode cover 127 for preventing the jet 126 from being sprayed on the needle electrode 8, as shown in FIG. 12. The shape of the needle electrode cover 127 is not particularly limited to a cylindrical shape surrounding the needle electrode 8 as shown in FIG. 12. For example, a sheet-like screen plate may be disposed on the upstream side of the needle electrode (that is, between the nebulization region and the needle electrode). Preferably, however, such a screen plate or needle electrode cover does not exist between the distal end of the needle electrode 8 and the electrode to which the ion intake orifice 111a opens, as shown in FIG. 12, so that corona discharge can be generated by applying a high voltage to the needle electrode 8.

Condensation of the solvent on the needle electrode can be prevented by the methods described with reference to FIGS. 10, 11 and 12. Therefore, even if the temperature of the metal block constituting the nebulization region and the vaporization region is lowered when a thermally unstable substance is analyzed, the discharge can be stably maintained and reliable analysis can proceed. By these measures, the safety problem of a short-circuit occurring between the needle electrode and the metal cover holding the needle electrode due to condensation or an over-current flowing there through can be avoided.

Further, the present invention can prevent condensation from occurring on the needle electrode. Therefore, analysis can be carried out stably for a long term even under the state where the temperatures of the nebulization region and the vaporization region are lowered, and safety can be improved because the short-circuit due to condensation on the needle electrode does not occur.

According to the present invention, the semi-micro liquid chromatograph having a velocity of the mobile phase of 0.1 to 0.2 ml/min can be connected to the mass spectrometer with substantially the same sensitivity as that of the conventional liquid chromatograph having a velocity of 1 ml/min. As a result, the present invention can provide a high sensitivity LC/MS apparatus.

While preferred embodiments have been set forth with specific details, further embodiments, modifications and variations are contemplated according to the broader aspects of the present invention, all as determined by the spirit and scope of the following claims.

We claim:

1. A mass spectrometer comprising means for supplying a sample solution consisting of a solvent and a solute, ionization means for ionizing said sample solution and means for analyzing the mass of ions generated by said ionization means, said mass spectrometer including:

a needle electrode for generating corona discharge; and a heater for heating said needle electrode.

2. A mass spectrometer according to claim 1, wherein the temperature of said needle electrode is higher than the boiling point of said solvent.

3. A mass spectrometer comprising means for supplying a sample solution consisting of a solvent and a solute, ionization means for ionizing said sample solution and means for analyzing a mass of ions generated by said ionization means, said mass spectrometer including:

a needle electrode for generating corona discharge;

means for maintaining said needle electrode being kept at a temperature higher than the boiling point of said solvent.

4. A mass spectrometer, comprising means for supplying a sample solution consisting of a solvent and a solute, nebulization means for nebulizing said sample solution, ionization means for ionizing said sample solution and means for analyzing a mass of ions generated by said ionization means, said mass spectrometer including:

a needle electrode for generating corona discharge; and a screen member for preventing a let of said sample solution formed by said nebulization means from reaching said needle electrode, wherein said screen member is an insulator containing therein said needle electrode.

5. A mass spectrometer, comprising:

a capillary for supplying a solution containing a sample;

a member for holding said capillary and a needle electrode for ionizing said sample-containing solution eluted from said capillary to provide ionized molecules, said holding member having a heater; and an analyzer region receiving said ionized molecules for conducting mass spectrometry of said ionized molecules of said sample;

wherein said capillary is inserted in a hole in said holding member and an insertion length is adjusted by a collar stoppper fit around a periphery of said capillary and engaging said holding member.

6. A mass spectrometer comprising means for supplying a sample solution of a solvent and a solute, an ionizer that ionizes vaporized molecules and an analyzing region that receives ionized molecules of a sample solution for conducting mass spectrometry of ionized molecules, said mass spectrometer including:

a needle electrode for generating corona discharge in said ionizer; and a heater for heating said needle electrode.

7. A mass spectrometer according to claim 6, wherein the temperature of said needle electrode is higher than a boiling point of said solvent.

8. A mass spectrometer comprising means for supplying a sample solution of a solvent and a solute, an ionizer that ionizes vaporized molecules and an analyzing region that receives ionized molecules of a sample solution for conducting mass spectrometry of ionized molecules, said mass spectrometer including:

a needle electrode for generating corona discharge;

means for maintaining said needle electrode being kept at a temperature higher than the boiling point of said solvent.

9. A mass spectrometer, comprising means for supplying a sample solution of a solvent and a solute, an ionizer that ionizes vaporized molecules and an analyzing region that receives ionized molecules of a sample solution for conducting mass spectrometry of ionized molecules, said mass spectrometer including:

a needle electrode for generating corona discharge; and a screen member for preventing a let of said sample from being blown into said needle electrode, wherein said screen member is an insulator containing therein said needle electrode.

10. A mass spectrometer comprising a supplier that supplies a sample solution consisting of a solvent and a solute, an ion source that ionizes said sample solution, and an analyzer that analyzes a mass of ions generated by said ion source, said mass spectrometer including:

a needle electrode for generating corona discharge; and a heater for heating said needle electrode.

11. A mass spectrometer according to claim 10, wherein the temperature of said needle electrode is higher than a boiling point of said solvent.

12. A mass spectrometer comprising a supplier that supplies a sample solution consisting of a solvent and a solute, an ion source that ionizes said sample solution, and an analyzer that analyzes a mass of ions generated by said ion source, said mass spectrometer including:

a needle electrode for generating corona discharge; and a heating portion to maintain said needle electrode to be kept at a temperature higher than a boiling point of said solvent.

13. A mass spectrometer, comprising a supplier that supplies a sample solution consisting of a solvent and a solute, a nebulizer that nebulizes said sample solution, an ion source that ionizes said sample solution, and an analyzer that analyzes a mass of ions generated by said ion source, said mass spectrometer including:

a needle electrode for generating corona discharge; and a screen member for preventing a jet of said sample solution formed by said nebulizer from reaching said needle electrode, wherein said screen member is an insulator containing therein said needle electrode.

* * * * *